United States Patent
Ong et al.

(10) Patent No.: US 6,174,732 B1
(45) Date of Patent: Jan. 16, 2001

(54) ANALYTICAL METHODOLOGY FOR QUALITATIVE AND QUANTITATIVE DETERMINATION OF CHEMICAL AGENT VAPOR

(75) Inventors: Kwok Y. Ong, Aberdeen; Jacob L. Barnhouse, Bel Air; Juan C. Cajigas, Edgewood, all of MD (US)

(73) Assignee: The United States of America as represented by the Secretary of the Army, Washington, DC (US)

(*) Notice: Under 35 U.S.C. 154(b), the term of this patent shall be extended for 0 days.

(21) Appl. No.: 09/152,478

(22) Filed: Sep. 10, 1998

(51) Int. Cl.[7] .................. G01N 1/18; G01N 1/00

(52) U.S. Cl. .............. 436/177; 436/161; 436/171; 436/178; 436/181; 422/68.1; 422/69; 422/88; 422/89; 73/23.41; 73/863.12; 73/1.02

(58) Field of Search .................. 73/863.12, 1.03, 73/23.41, 863.11; 436/177, 161, 171, 178, 181; 422/68.1, 69, 88, 89

(56) References Cited

U.S. PATENT DOCUMENTS

| | | | |
|---|---|---|---|
| 4,069,701 | * | 1/1978 | Baldauf et al. .................... 73/1 G |
| 4,269,057 | * | 5/1981 | Ong et al. .......................... 73/1 G |
| 4,399,688 | * | 8/1983 | Dennis .............................. 73/23.1 |
| 5,014,541 | * | 5/1991 | Sides et al. ...................... 73/23.41 |
| 5,052,805 | * | 10/1991 | Sides ................................ 356/315 |
| 5,305,630 | * | 4/1994 | Molozay et al. ................. 73/1 G |
| 5,728,927 | | 3/1998 | Ong . |
| 5,792,663 | * | 8/1998 | Fry et al. ............................ 436/73 |
| 5,970,803 | * | 10/1999 | Staples et al. ................. 73/863.12 |

* cited by examiner

Primary Examiner—Jill Warden
Assistant Examiner—Patricia Kathryn Bex
(74) Attorney, Agent, or Firm—Ulysses John Biffoni; Vincent J. Ranucci

(57) ABSTRACT

A method for producing and sampling chemical agent vapor comprising the steps of placing neat chemical agent in a reservoir, purging the chemical agent in the reservoir with a dry air, and analyzing the air stream exiting the reservoir. A MINICAMS having a removable PCT may be used to analyze the air stream exiting the reservoir. The method may further comprise the steps of changing the relative humidity conditions and testing chemical agent detectors.

**19

GC CHROMATOGRAM

THIOLAMINE

MINICAMS CHROMATOGRAM
DIRTY VX (DRY)

VX PEAK

VOLTS

SECONDS

FIG. 2B

GC CHROMATOGRAM

VX

THIOLAMINE

FIG. 3A

MINICAMS CHROMATOGRAM
SEMI-PURE VX SAMPLE

VX PEAK

VOLTS

SECONDS

FIG. 3B

GC CHROMATOGRAM

VX

THIOLAMINE

FIG. 4A

MINICAMS CHROMATOGRAM
CLEAN VX (DRY)

VX PEAK

VOLTS

SECONDS

DIRTY VX (DRY) — VX PEAK

FIG. 5B

DIRTY VX (WET) — VX PEAK

FIG. 5C — CLEAN VX (DRY); VX PEAK

FIG. 5D — CLEAN VX (WET); VX PEAK

ANALYTICAL METHODOLOGY FOR QUALITATIVE AND QUANTITATIVE DETERMINATION OF CHEMICAL AGENT VAPOR

GOVERNMENT INTEREST

The invention described herein may be manufactured, licensed, and used by or for the U.S. Government.

BACKGROUND OF THE INVENTION

1. Field of the Invention

The present invention relates to the qualitative and quantitative determination of chemical agents. More particularly, the present invention is a method for determining O-ethyl S-(2-diisopropylanimoethyl) methylphosphonothiolate, better known as VX, vapor. Most particularly, this invention permits the generation of a purer non-contaminated VX vapor and the analytical determination of the VX samples collected under various relative humidity conditions.

2. Brief Description of the Related Art

O-ethyl S-(2-diisopropylanimoethyl) methylphosphonothiolate, better known as VX, is an extremely toxic chemical warfare agent. It is a relatively stable compound that undergoes slow degradation. For example, the non-stabilized VX of 95% purity, without adding a compound stabilizer, decomposes at a rate of approximately 5% per month at 25° C. The decomposition impurities include ethyl methylphosphonic acid, methylphosphinic acid, diisopropylaminoethyl mercaptan, diethyl methylphosphonate, and ethanol.

As an extremely toxic compound, VX detection is best accomplished at the lowest possible concentration. Chemical detectors used for the detection of VX require calibration. Vapor samples of a known concentration of VX are used to test and evaluate these detectors. The VX samples need to be qualitatively pure and quantitatively analyzed to be useful in properly evaluating different chemical agent detectors.

Pure VX samples, of 95% or greater (CASARM quality), are useful in testing chemical agent detectors. CASARM (Chemical Agent Standard Analytical Reference Materiel) VX is used for instrument calibration to provide truest reference. Compound stabilizer is not added within the neat VX sample. However impurities within the VX sample itself, such as at approximately 5%, affect detector testing in a disproportionate manner. Volatility differences between VX and accompanying impurities within a sample produce vapors that are not representative of the respective amounts of VX and impurities within the liquid sample. Greater vaporization rates of the impurities produce a vapor saturated with impure vapors during the initial vaporization of the VX sample. Impurities contained in a VX sample which are more volatile than VX, interfere with most chemical detectors as well as most analytical methodologies. As the amount of impurities within the VX sample decreases, an increase in the reliability of the testing of chemical agent detectors occurs. For example, 95% pure VX samples, having impurities such as diisopropylaminoethyl mercaptan (thiolamine) at 5%, produce vapors containing less than 1% VX vapor and greater than 99% thiolamine vapor. As such, these impurities cause significant interference with testing most chemical detectors as well as most analytical methodologies. As discussed above, although an impurity may only exist in small percentage in the liquid VX sample, it may become the major constituent in the vapor mixture when vaporized. For proper VX vapor evaluation of detection devices and analysis, elimination of non-VX impurities (such as thiolamine) is necessary.

Several methods have been used to quantify a VX vapor sample. The Shoenemann reaction determines VX concentration by converting the VX into a G-agent analog before reacting with indole and peroxide to produce a fluorescence reaction. However, the reaction is interfered with by the existence of excess thiolamine. The thiolamine interferes with precipitate filtration as well as affecting the fluorescence reading of the sample. Thus, thiolamine may cause fluorescence false readings that affect the actual VX vapor concentration.

The presence of thiolamine also affects the outcome of the enzymatic method of analysis, which was developed to substantially negate the thiolamine effect. The lengthy enzymatic method requires detailed knowledge in the use and maintenance of the complex equipment. The enzymatic method also results in the generation of significant amounts of waste solution, requiring extensive disposal procedures. Additionally, the enzyme method does not distinguish the effects from other impurities in the VX vapor sample, nor identify the relative abundance of the impurities present.

Analysis by a gas chromatographic method, using a solvent containing bubbler to collect a vapor sample, provides a separation identification of the impurity vapors from the VX vapors. The method draws and collects the vapor into a solvent, only a small portion of which (approximately 5 microliters of a 5 milliliter sample) is then injected into a gas chromatograph (GC) equipped with a flame photometric detector (FPD). The VX peak, separated from the impurity peaks, is used to determine the VX vapor concentration. Because of the injection limitations, the gas chromatographic method has limited detection capability of approximately 0.04 $mg/m^3$ of VX concentration or greater. The accuracy and reliability of the method are compromised from the combined affects of factors such as long sampling times of five to ten minutes, collection efficiency, solvent evaporation, and small sample injection. The method, although effective for analyzing VX vapor at low relative humidity conditions, is unable to analyze VX vapor sample collected under high humidity conditions. When used under high humidity conditions, the VX peak may be lost or substantially diminished from an expected concentration.

Also known in the art, VX vapor may be analyzed using the Miniaturized Continuous Air Monitoring System (MINICAMS), described in U.S. Pat. No. 5,014,541 (Sides et al.) and U.S. Pat. No. 5,052,805 (Sides), which issued on May 14, 1991 and Oct. 1, 1991, respectively. It provides a method of detecting VX vapor by passing the VX vapor through a conversion pad that converts the VX vapor into a more volatile G-analog similar to the conversion process of the fluorescence method, described above. Conversion efficiencies are affected by the age of the conversion pad, the temperature and humidity, the flow rate through the pad, impurities and other factors. The MINICAMS' FPD detector detects the converted G agent analog peak, thereby deriving an equivalent VX concentration. Such MINICAMS method is not useful for precise quantitative and qualitative analysis because of the quality of the conversion pads and the unknown effects from the associated impurity vapors. Additionally, such MINICAMS method lacks the ability to separate or distinguish the relationship between the impurities and VX.

In addition to low volatility, VX readily adheres to most surfaces contacted. As such, low concentrations of VX sample are significantly reduced when transferred through any additional tubing or connections. This reduction significantly interferes with conventional methods in quantifying VX agent vapors for testing chemical agent detectors.

In view of the foregoing, improvements in chemical monitoring have been desired. It has been desired to provide an improved methodology for sampling VX both quantitatively and qualitatively.

SUMMARY OF THE INVENTION

The present invention provides a method for generating and sampling chemical agent vapor comprising the steps of placing liquid chemical agent in a reservoir, maintaining the reservoir at a sufficient temperature to vaporize contaminants within the chemical agent; purging the contaminant vapor with dry air, wherein the dry air removes contaminant vapor from the reservoir while retaining the chemical agent in the reservoir, adjusting the temperature of the reservoir sufficient to form vapor from the retained chemical agent; flowing conditioned air over the vaporizing retained chemical agent, wherein conditioned air mixes with and carries the chemical agent vapors from the reservoir to a sample port; and, analyzing the mixture of conditioned air and chemical agent vapors at the sample port.

BRIEF DESCRIPTION OF DRAWINGS

FIG. 2A is a GC chromatogram of a VX sample containing significant impurities;

FIG. 2B is a MINICAMS chromatogram of a VX sample containing significant impurities;

FIG. 3A is a GC chromatogram of a VX sample containing slight impurities;

FIG. 3B is a MINICAMS chromatogram of a VX sample containing slight impurities;

FIG. 4A is a GC chromatogram of a pure VX sample of the present invention;

FIG. 4B is a MINICAMS chromatogram of a pure VX sample of the present invention;

FIG. 5A is a MINICAMS chromatogram of a VX sample containing significant impurities under dry relative humidity conditions;

FIG. 5B is a MINICAMS chromatogram of a VX sample containing significant impurities under wet relative humidity conditions;

FIG. 5C is a MINICAMS chromatogram of a pure VX sample under dry relative humidity conditions of the present invention; and, FIG. 5D is a MINICAMS chromatogram of a pure VX sample under wet relative humidity conditions of the present invention.

DETAILED DESCRIPTION OF THE PREFERRED EMBODIMENTS

Figure 1:
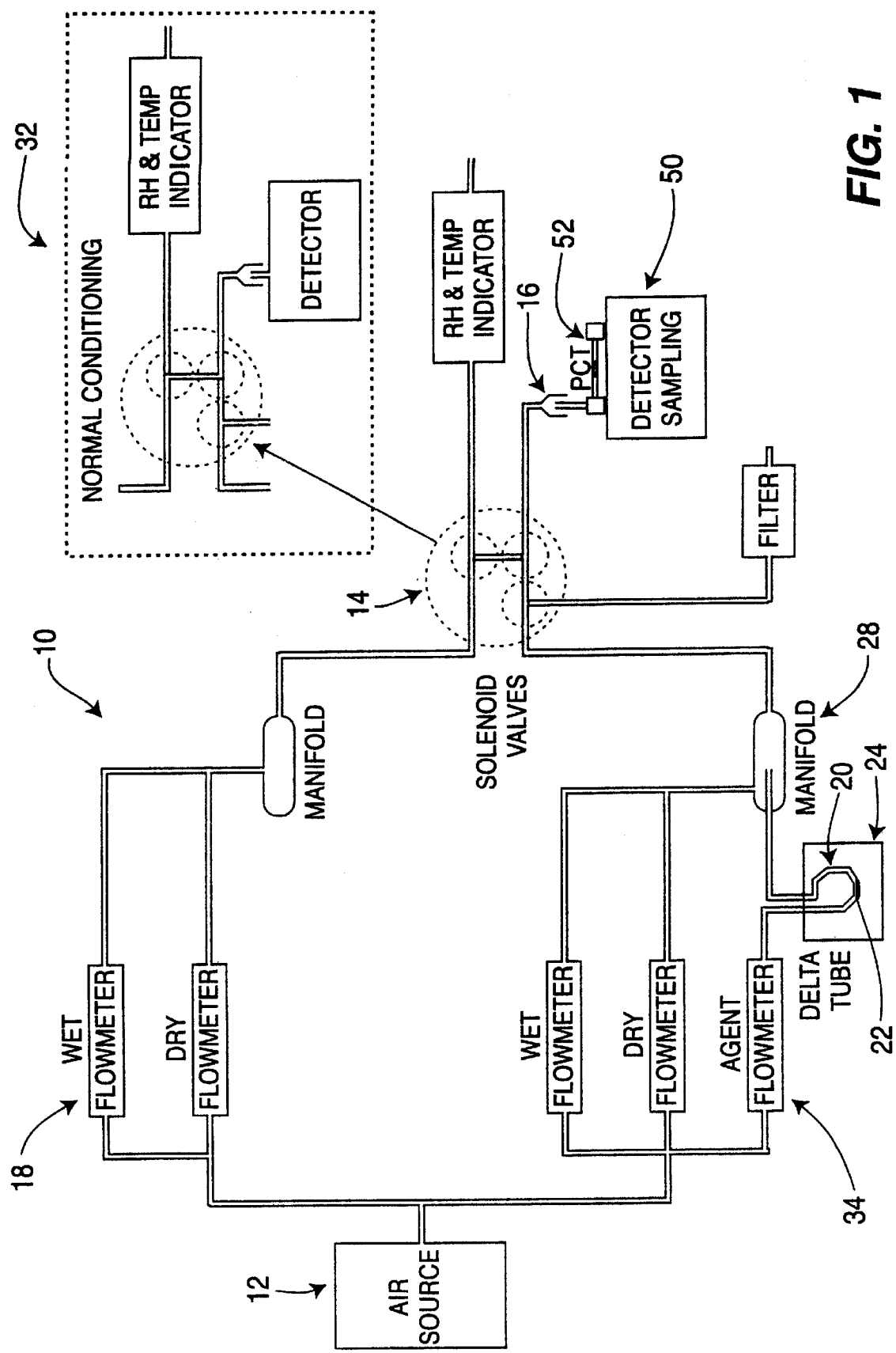
FIG. 1 illustrates an agent generation system comprising a delta tube and MINICAMS chemical monitoring system.

The present invention provides a method for generating vapors from low volatility chemical compounds, such as Sarin (GB), Tabun (GA), Soman (GD), Distilled Sulfur Mustard (HD), Nitrogen Mustard (HN3), Lewisite (L), and O-ethyl S-(2-diisopropylanimoethyl) methylphosphonothiolate (VX) agent, and/or other like compounds, and sampling those vapors. Preferably, the present invention is a method for generating and sampling pure VX agent samples regardless of the humidity conditions. The methodology provides for the purification of VX agent sample within a delta tube, and later vapor analysis of that sample using a MINICAMS as the analytical instrument. A stream of dry air is swept over a small drop of liquid VX sample which contains thiolamine and other higher volatile impurities in the delta tube. The thiolamine and other higher volatile impurities are gradually purged. The purged VX sample becomes a pure or clean VX agent. The pure VX agent vapor is transferred directly from the delta tube into a manifold where it is mixed with a conditioned air at a specific relative humidity (RH) to form a targeted VX vapor concentration. The MINICAMS uses GC-FPD (Flame Photometric) detector for VX detection directly without the need to convert the VX into its more volatile G-analog.

As seen in FIG. 1, a vapor generating apparatus 10 is shown having a delta shaped tube 20 which is used as the chemical agent reservoir. The vapor generating apparatus 10 generates a gas concentration to test chemical agent detectors. The generated gas sample is analyzed to provide a known concentration and purity for proper testing of the detectors.

A chemical agent 22 sample, in this case VX agent, is used in the vapor generating apparatus 10 The VX agent 22 sample usually contains small amounts of impurities. Preferably, the VX agent 22 sample has a high purity of 95% or greater VX agent 22, more preferably from about 98% or greater VX agent 22, and most preferably from about 99.5% or greater VX agent 22. The VX agent 22 is placed into the delta tube 20, and the delta tube 20 is then placed into a temperature bath 24. The amount of the VX agent 22 sample may be any measurable amount which may be supported within the delta tube 20 while allowing the delta tube 20 to properly function. Preferably the sample amount of the liquid VX agent 22 is from about 10 microliters to 150 microliters, more preferably from about 10 microliters to 100 microliters, and most preferably from about 10 microliters to about 50 microliters. Smaller samples require shorter purging time to achieve clean VX. The delta tube 20 maintains the agent 22 at a constant temperature by immersion in the temperature bath 24, which evaporates or vaporizes the impurities within the VX agent 22 in the delta tube 20 during a purging phase of the VX agent 22 sample. Additionally, the temperature bath 24 maintains the VX sample at a constant temperature to provide a stable vapor concentration for use during the detector testing phase.

During the purging phase, the temperature bath 24 is maintained at a temperature that permits the vaporization of impurities within the VX agent 22 sample without decomposing the VX agent 22. Preferably during the purging phase, the temperature bath 24 is maintained at a temperature of from about 20° C. to about 100° C., more preferably from about 25° C. to about 75° C., and most preferably from about 35° C. to about 45° C. Vaporization is achieved while minimizing potential condensation at other parts of the apparatus during the process.

The constant temperature of the temperature bath 24 provides a constant vapor within the delta tube 20 resulting from the evaporation of the VX agent 22 sample. This vapor comprises gases from the VX agent 22, as well as vapors from impurities within the agent 22. The extremely low volatility of the VX agent 22 in comparison to the impurity components, provides a resultant vapor disproportionately comprised of vapors from the impurities in the VX agent 22 sample. As long as the low volatile VX agent 22 evaporates at a significantly slower rate than the impurities within the VX agent 22 sample, the vapors within the delta tube 20 will contain a significantly greater proportion of vapor from the impurities. VX agent 22 has a volatility that can be determined from the Antoine vapor pressure estimation using the formula log Pressure$_{(torr)}$=7.2810−[2072.1/(172.54+ temperature$_{(degrees\ C)}$)]. Using the equation, VX at a temperature of 18° C. at one atmosphere has a volatility of approximately 3.72 mg/m³. At 20° C., VX has a volatility of approximately 4.81 mg/m³. At 25° C., VX has a volatility of approximately 8.86 mg/m³. As the vapors are created in the delta tube 20 with the constant temperature of the temperature bath 24, the delta tube 20 is also purged with air 12. The more volatile impurities within the sample are purged from the sample at a greater rate than VX agent. After sufficient purge time, the impurities have been removed, and the sample comprises purified VX agent 22.

The purification of the VX agent 22 provides a final purity of the agent 22 which is proportional to the flow rate, the initial purity of the starting sample, the temperature of the sample, and the type of impurities within the sample. The purge air 12 may be any dried carrier gas that permits the purging of the impurity vapors from the delta tube 20. This includes, but is not limited to, atmospheric air, nitrogen, helium, and the like. The purge air 12 comprises a sufficiently low humidity and is sufficiently clean or filtered as to not contaminate the VX agent 22 within the sample during purging. The dry air 12 preferably has a moisture content of from about 5% or less, more preferably from about 2% or less, and most preferably from about 0.5% or less. The purge air 12 flow rate comprises any rate which permits efficient purging of the impurity vapors from the sample, preferably from about 20 cm³/min to about 300 cm³/min, more preferably from about 50 cm³/min to about 250 cm³/min, still more preferably from about 100 cm³/min to about 200 cm³/min, and most preferably from about 150 cm³/min to about 175 cm³/min. The duration or time of purge air 12 comprises any time period which efficiently purges the impurities from the sample, preferably from about 30 minutes to about 2 days, more preferably from about 2 hours to about 1 day, still more preferably from about 3 hours to about 12 hours, and most preferably from about 4 hours to about 5 hours.

After the VX agent 22 sample is purged, the VX agent 22 is heated to a temperature sufficient to create VX agent 22 vapors in the delta tube 20. Conditioned air is flowed through the delta tube 20, mixing with the VX agent 22 vapors and carrying the vapors out of the delta tube 20 reservoir to an outlet or sample port 16. Conditioned air comprises air that is filtered, and adjusted to proper relative humidity conditions, which may be either high or low. The relative humidity of the conditioned air is varied by circulating the conditioned air through flowmeters 34. Conditioned air may be any gas which does not interfere with the transfer of the VX agent 22 vapors to the sample port. Preferably, the conditioned air comprises an inert gas. More preferably, the conditioned air comprises nitrogen, argon, or helium. Most preferably, conditioned air comprises nitrogen.

Once the VX agent 22 sample is purged, and the vapor is mixed with conditioned air, the resultant vapor sample is collected into the pre-concentrator tube (PCT) of the Miniaturized Continuous Air Monitoring System (MINICAMS) 50 for concentration determination. As further seen in FIG. 1, the MINICAMS 50 comprises a periodic monitoring system for the generated VX vapor. Although the MINICAMS 50 is a known type of chemical detection device, it is modified within the present invention to serve as an analytical instrument for samples collected from the vapor generating apparatus 10. The MINICAMS 50 analyzes the VX agent 22 vapor flowing out of the vapor generating apparatus 10, providing a concentration value for the exiting vapors which is used to calibrate other chemical detectors.

Generally, the MINICAMS 50 is first calibrated with known samples of VX agent 22 to develop a calibration curve. The calibration curve is formed from plotted peak height values of respective chromatograms against the relative amount of VX to derive a standard calibration curve. Once plotted, the slope of the calibration curve is used to calculate the amount of VX agent 22 contained in the PCT sample collected from the vapor generating apparatus 10 to arrive at an equivalent vapor concentration. The chromatograms obtained from MINICAMS 50 on sequential samples are used to determine the relative purity of the VX agent 22 vapors derived from a given VX agent 22 sample within the delta tube 20 to monitor the purging progress.

The configuration of the MINICAMS 50 requires a sample vapor to pass through an inlet check valve and an inlet heater block before reaching the concentrating sorbent tube, known as PCT, 52. Preferably, the sorbent of the PCT 52 is solid and has the ability to adsorb the sample vapor constituents. For low volatility compounds, such as VX agent 22, substantial amounts of the vapor sample adhere to the valves and tubing before reaching the PCT 52 for subsequent desorption and analysis. The method of the present invention modifies the sampling routine of the MINICAMS by using a manual sampling technique to by-pass the inlet check valve and inlet heater block to collect the sample directly from the generating apparatus 10 into the PCT 52.

This manual sampling technique requires disconnecting the PCT 52 from the MINICAMS 50 prior to collecting the VX agent 22 vapor. The PCT 52 is placed directly across the sample port 16 of the vapor generating apparatus 10. A vacuum source draws on the opposite side of the PCT 52 from the sample port 16, using such vacuum devices as a vacuum pump, suction ball or the like. The amount of suction may be any known amount that allows proper transfer of the VX agent 22 into the PCT 52. Preferably the suction is from about 0.01 liters/minute to about 1.0 liters/minute, more preferably from about 0.05 liters/minute to about 0.5 liters/minute, and most preferably from about 0.1 liters/minute to about 0.3 liters/minute. The VX agent 22 within the air flow in the vapor generating apparatus 10 is drawn directly in and absorbed into the sorbent bed of the PCT 52. The temperature of the PCT 52 is such as to allow the adsorption of the VX agent 22 into the PCT 52. Preferably, the temperature of the PCT 52 is from about 0° C. to about 60° C., more preferably from about 20° C. to about 50° C., and most preferably from about 25° C. to about 35° C. By using the direct transfer of the present invention from the vapor generating apparatus 10 into the PCT 52, VX agent 22 does not attach to tubing and/or other components within the MINICAMS 50, which would contaminate the MINICAMS' inlet system and prevent the sample from reaching the sorbent material of the PCT 52.

Once the agent 22 is transferred into the PCT 52, the PCT 52 is re-inserted within the MINICAMS 50. Once the PCT 52 containing the VX agent 22 is in the MINICAMS 50, the VX agent 22 is purged for an additional period of time. A stream of zero air is passed through the sorbent in the PCT 52 which allows purging the trapped moisture when the VX agent 22 sample is collected in humid condition. The sorbent, by design, will retain the trapped VX and allow the moisture to evaporate. Generally, the zero air flows in a direction away from the gas chromatographic column within the MINICAMS 50 during its sampling cycle. Zero air comprises air which is clean and dry. Zero air includes any gas or gases known as air constituents, such as nitrogen, argon, helium, and other like inert gases, and combinations thereof. Preferably the zero air comprises an inert gas, and more preferably the zero air comprises nitrogen. Preferably, the zero air is filtered and dried atmospheric air. More preferably, the zero air has been filtered, dried, and chemically purified, and most preferably the gas is provided from a pure air generator. Additionally, preferably the zero air is dried to a relative humidity of from about 10% or less, more preferably from about 5% or less, and still more preferably from about 1% or less, and most preferably from about 0.5% or less. The time period of purging the PCT 52 containing the VX agent 22 in the MINICAMS 50 varies with the estimated moisture content. Preferably, zero air is swept across and purges the VX agent 22 for a time period of from about 30 seconds to about 300 seconds, more preferably from about 60 seconds to about 200 seconds, and most preferably from about 120 seconds to about 150 seconds.

After the zero air purges the moisture from the sorbent in the PCT 52, the PCT 52 is heated and a suitable carrier gas, such as nitrogen, is swept across the PCT 52. The carrier gas provides a carrier to the VX agent 22 vapor to flow into the gas chromatographic column as it eludes from the heated PCT 52. Preferably the PCT 52 is heated to a temperature of from about 40° C. to about 250° C. for 215 seconds, more preferably from about 50° C. to about 250° C. for 210 seconds, and most preferably from about 60° C. to about 240° C. for 200 seconds. The carrier gas comprises any gas which permits the VX agent 22 to be carried into the gas chromatographic column and which does not interfere with the workings of the gas chromatographic column. Preferably, the carrier gas comprises nitrogen gas or helium gas. More preferably, the carrier gas comprises nitrogen gas. The flow rate of the carrier gas is fixed which permits proper elution of the VX agent 22 through the gas chromatographic column. Preferably, the flow rate of the carrier gas is regulated by the carrier gas pressure from 35 psi to 50 psi more preferably from about 40 psi to 45 psi, and most preferably from about 40 psi to 42 psi.

The VX agent 22 is separated from any impurities in the gas chromatographic column and is detected both qualitatively and quantitatively by the Flame Photometric Detector (FPD). The VX agent 22 is qualified by peak separation of the VX agent 22 from sample impurities within the gas chromatographic column. The gas chromatographic flame photometric detector (GC-FPD) within the MINICAMS derives the chromatogram. The VX agent 22 is quantified by measuring the VX agent 22 peak indicated in the gas chromatographic trace of the sample, from which a determinable amount of VX agent 22 may be calculated based on the calibration curve using known amounts of standard solutions.

The method of the present invention produces a gradual cleansing of the VX samples, and eventually achieves a highly purified VX stage that produces non-contaminated (highly purified) VX vapor. With the non-contaminated VX agent 22, the present invention permits analytical calibration of the vapors generated within the vapor generating apparatus 10. Once the generated vapor is calibrated, the correct testing and evaluation of VX vapor detectors 50 using the vapor generating apparatus 10 is possible.

After the vapor produced by the vapor generating apparatus 10 is calibrated, chemical agent detectors 50 are tested.

As seen in FIG. 1, the flow rate and humidity are controlled within the vapor generating apparatus 10 through solenoid assembly 14 to the detector sample port 16. The VX agent 22 vapors may be diluted to the desired concentration and humidity conditions to provide proper realistic detector testing by the following process. The vapor generating apparatus 10 provides a chemical agent stream diluted to the desired concentration at controlled humidity condition. Additionally, a paralleled conditioning stream 18 of air without the chemical agent exists which has similarly controlled humidity condition as the chemical agent stream. The vapor generating apparatus 10 is regulated to provide the desired relative humidity and concentration. The concentration is proportional to the flow rate over the VX agent 22, the flow rate of the mixing gases in a manifold 28, and the temperature of the temperature bath 24. Chemical agent detectors 50 are attached to the sample port 16 and tested for the given relative humidity and concentration conditions. After a series of chemical agent detectors 50 are tested or challenged, the relative humidity and concentration within the vapor generating apparatus 10 may be changed to provide testing for different concentrations and amounts of relative humidity. After the relative humidity and concentration are varied, the vapor generating apparatus 10 is re-calibrated by analyzing the VX agent 22 vapor sample once again with the method of the present invention, as previously described. During the chemical agent detector 50 testing phase, the detectors 50 and the portion of the apparatus 10 after the mixing manifolds 28, may be placed in an environmental chamber 32 set at any temperature which permits testing of the chemical agent detectors 50 as required, which is an amount equivalent to the VX sample 22 vaporized within the delta tube 20. Preferably, the chamber 32 temperature is from about −10° C. to about +52° C., more preferably from about 0° C. to about +45° C., and most preferably from about +20° C. to about +30° C. according to the test requirements.

FIGS. 2A and 2B show GC chromatograms of a VX sample for a freshly charged generator vapor sample. The chromatograms show significant impurities on the GC chromatograms where the impurities overwhelm the VX data. However, the GC chromatogram of FIG. 2A shows the less volatile VX agent 22 coming off the column at a later time than the impurities within the sample. The impurities contain such compounds as thiolamine. Similarly, the MINICAMS chromatogram trace in FIG. 2B shows the same impure VX sample, and also indicates a separate peak for VX agent, with the impurities interfering with the VX agent GC trace.

A VX agent 22 sample which has been purged for a period of time is shown in FIGS. 3A and 3B. FIG. 3A shows a standard GC chromatogram of the VX sample containing slight impurities. The impurities do not interfere with the VX agent 22 trace as shown in FIGS. 2A and 2B. FIG. 3B shows a MINICAMS chromatogram trace of a VX sample containing slight impurities similar to FIG. 3A. The relatively clean VX agent 22 sample provides for a better qualitative and quantitative analysis of the VX agent 22 within the sample.

FIGS. 4A and 4B show the VX agent sample after an extended purging time period. The very clean VX agent within the sample contains minuscule amounts of impurities. FIG. 4A shows a standard GC chromatogram trace of a pure VX sample. FIG. 4B shows a MINICAMS chromatogram trace of the same pure VX sample.

Figures 5A, 5B:
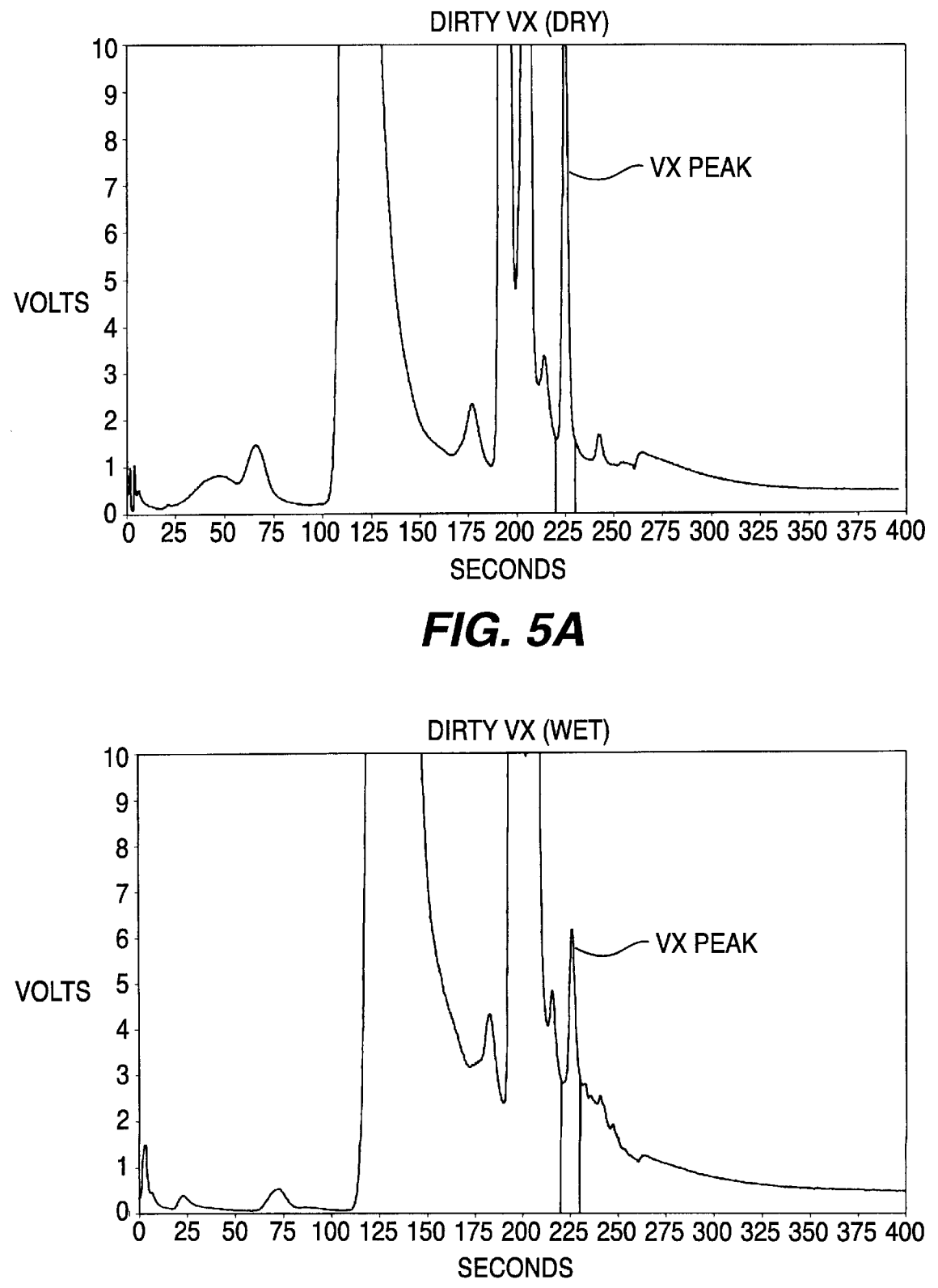
Figures 5C, 5D:
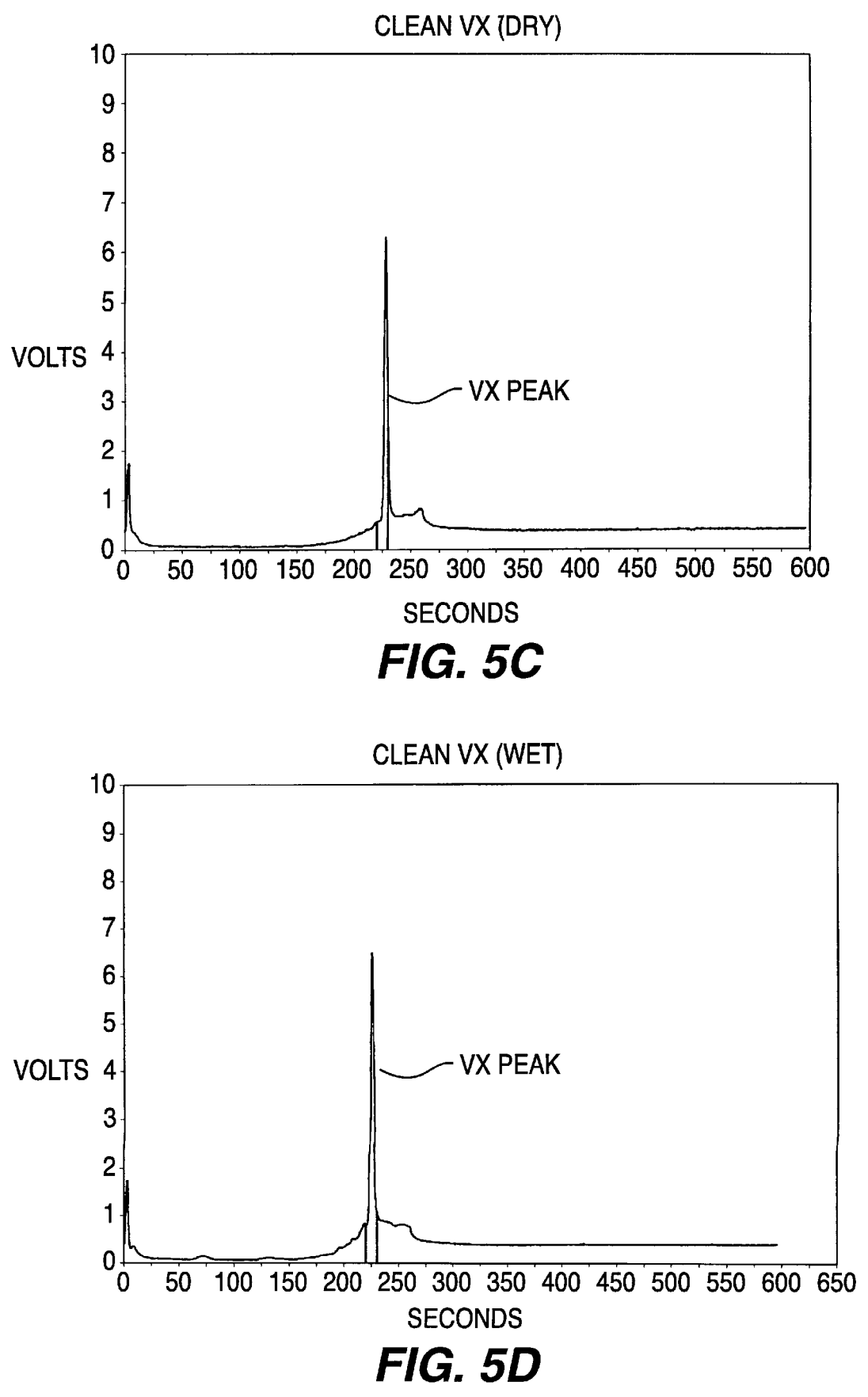

FIGS. 5A–5D show various VX agent 22 samples under dry and wet relative humidity conditions. As seen in FIG. 5A, a MINICAMS chromatogram of a VX agent 22 sample containing significant impurities under dry relative humidity conditions is extremely cluttered, obscuring the VX peak. In FIG. 5B, a MINICAMS chromatogram of a VX agent 22 sample containing significant impurities under wet relative humidity conditions also is extremely cluttered. However in FIG. 5C, a MINICAMS chromatogram shows a pure VX agent 22 sample under dry relative humidity conditions. The sample shown in 5C has undergone the method of the present invention. The VX agent 22 sample is clearly distinguishable, and easily qualified and quantified. Additionally, the MINICAMS chromatogram of a pure VX sample under wet relative humidity conditions shown in FIG. 5D also has undergone the method of the present invention. FIG. 5D shows readily identifiable VX agent 22 without interference from impurities within the sample.

In operation, the method of the present invention provides analysis of VX agent 22 in high relative humidity conditions. VX agent 22 vapor which is collected under high humidity conditions is dried by allowing additional drying time during the sampling cycle of the MINICAMS using the zero air after the manually collected sample in the PCT 52 is returned to the MINICAMS before the heat desorption begins. As seen in FIG. 5D, the high relative humidity VX agent 22 sample shows a separation from the associated impurities, indicating an effective analytically method.

The method of the present invention allows detection of from about $1-2\times10^{-9}$ grams of VX agent 22 or less. The concentration of VX agent 22 vapor detectable varies depending on the sampling rate and time. For example, a sampling rate of 500 cc/min for 1 min that yield a peak height equivalent to $1\times10^{-9}$ g would equate to a vapor concentration of $1\times10^{-9}$ g/0.5 liter which equals to $2\times10^{-3}$ mg/m$^3$. The method may also be used as verification of compound volatility at very low temperatures and for compounds that have very low volatility because if its direct sample deposit and relative sensitivity. The method is particularly useful in compounds having a great affinity to surface adsorption, such as VX agent 22.

EXAMPLE 1

To generate the VX vapor sample, VX agent was placed into a delta tube, while ensuring the amount of VX liquid did not block the diameter of the tube. The delta tube was connected to a vapor generator, using the method described in U.S. Pat. No. 5,728,927 (Ong), which issued on Mar. 17, 1998, the disclosure of which is herein incorporated by reference. A MINICAMS' PCT was placed at the sample port of the vapor generator, and a vacuum source was connected to the opposite end of the PCT. A sample from the vapor generator was collected manually by running the vacuum source at a known flow rate over a recorded time period. Once the sample was collected, the PCT was placed into the MINICAMS for analysis of the vapor sample. A calibration curve was derived using a MINICAMS chemical agent detector as an analytical device. The calibration curve was done by plotting the chromatographic peak heights of various concentrations of known amount of VX agent samples against the relative amount of VX, shown in Tables 1 and 2 below. Table 1 shows a VX calibration curve using different amounts of VX agent in an alcoholic solution at a known concentration of 5.1 ng/µl. Once plotted, the slope of the calibration curve is useful to calculate the amount of VX agent contained in the sample collected from the vapor generator to arrive at an equivalent vapor concentration as shown in Table 2 and Example 2.

TABLE 1

| Amount Deposited in PCT (microliter) | VX Standard Concentration (nanogram/microliter) | Total VX Dosage (nanogram) | VX Peak Height (units) |
|---|---|---|---|
| 1 | 5.1 | 5.1 | 516 |
| 2 | 5.1 | 10.2 | 1090 |
| 3 | 5.1 | 15.3 | 1479 |
| 4 | 5.1 | 20.4 | 1935 |

Table 2 shows several VX vapor calibration of samples from the generator at different RH conditions using sampling flow rate of 500 cc/min for 30 seconds.

TABLE 2

| AGENT Sample Volume Time × Rate (m$^3$) | Peak Height Units | Equivalent Agent (nanogram) | Derived Vapor Concentration (mg/m$^3$) |
|---|---|---|---|
| $2.5 \times 10^{-4}$ | 1167 | 12 | 0.047 mg/m$^3$ |
| $2.5 \times 10^{-4}$ | 808 | 7.5 | 0.030 mg/m$^3$ |
| $2.5 \times 10^{-4}$ | 477 | 4 | 0.016 mg/m$^3$ |
| $2.5 \times 10^{-4}$ | 661 | 6 | 0.024 mg/m$^3$ |

EXAMPLE 2

0.1 ml of VX liquid, having a purity of greater than 95%, was placed into a delta tube, while ensuring the amount of VX liquid did not block the diameter of the tube. The delta tube was connected to a vapor generator, using the method described in U.S. Pat. No. 5,728,927 with the temperature bath at 18° C. The VX agent was swept at a flow rate of 40 cm$^3$/min after being purged. The air exited from the delta tube was mixed with 3.5 liters of conditioned air, yielding a total of 3.540 liters at the sample port. A MINICAMS' PCT was placed at the sample or outlet port of the vapor generator, and a vacuum source was connected to the opposite side of the PCT. A sample from the vapor generator was collected manually by running the vacuum pump at a flow rate of 0.5 liter/minute over a time period of 0.5 minutes. Once the 0.25 liter sample was collected, the PCT was placed into the MINICAMS for analysis. The chromatographic peak representing the amount of VX agent within the sample was referenced against the calibration curve of example 1, and the concentration of the VX agent was calculated to equal to 8.09 nanograms. By calculation, the amount of VX vapor exiting from the delta tube reservoir equaled to 114.55 nanograms. Previous calculations indicated that such amount represented a volatility of the VX sample of 2.86 mg/m$^3$ experimentally derived as compared to the theoretical calculated value of 3.73 mg/m$^3$. It showed that a sweeping efficiency at 40 cc/min over a small drop of VX through the delta tube was approximately 76.6%, demonstrating the reliability of the present invention.

It should be understood that the foregoing summary, detailed description, examples and drawings of the invention are not intended to be limiting, but are only exemplary of the inventive features which are defined in the claims.

What is claimed is:

1. A method for generating and sampling chemical agent vapor, comprising the steps of:
   placing liquid chemical agent in a reservoir;
   maintaining the reservoir at a sufficient temperature to vaporize contaminants within the chemical agent;
   purging the contaminant vapor with dry air, wherein the dry air removes contaminant vapor from the reservoir while retaining the chemical agent in the reservoir;

adjusting the temperature of the reservoir sufficient to form vapor from the retained chemical agent;

flowing conditioned air over the vaporizing retained chemical agent, wherein conditioned air mixes with and carries the chemical agent vapors from the reservoir to a sample port;

analyzing the mixture of conditioned air and chemical agent vapors at the sample port, said analyzing comprising the further steps of:

providing a MINICAMS having removable PCT, wherein the PCT is separated from the MINICAMS;

transferring the mixture of conditioned air and chemical agent vapors into the PCT;

placing the PCT having the transferred chemical agent into the MINICAMS;

sweeping the transferred chemical agent in the PCT with zero air;

heating the PCT, wherein the chemical agent is desorbed;

flowing a carrier gas across the heated PCT, wherein the desorbing chemical agent is mixed with the carrier gas; and measuring a chromatographic elution of the chemical agent within the carrier gas.

2. The method of claim 1, wherein the chemical agent comprises a low volatility compound.

3. The method of claim 2, wherein the chemical agent comprises a toxic chemical compound selected from the group consisting of Sarin (GB), Tabun (GA), Soman (GD), Distilled Sulfur Mustard (HD), Nitrogen Mustard (HN3), Lewisite (L), and VX agent.

4. The method of claim 3, wherein the chemical compound comprises VX agent.

5. The method of claim 4, wherein VX agent is from about 95% pure or greater when placed into the reservoir.

6. The method of claim 1, wherein the reservoir containing the chemical agent is maintained at a constant temperature.

7. The method of claim 6, wherein the constant temperature is from about 20° C. to about 100° C.

8. The method of claim 1, wherein analyzing the mixture of conditioned air and chemical agent further comprises gas chromatography analysis.

9. The method of claim 1, wherein flow rate of the purging dry air is from about 20 $cm^3$/min to about 300 $cm^3$/min.

10. The method of claim 1, wherein the flow rate of the conditioned air is from about 20 $cm^3$/min to about 1000 $cm^3$/min.

11. The method of claim 1, wherein the duration of the purging dry air is from about 30 minutes to about 2 days.

12. The method of claim 9, wherein the step of analyzing the mixture comprises a sampling time of from about 5 seconds to about 30 minutes.

13. The method of claim 1, further comprising the step of calibrating the MINICAMS.

14. The method of claim 1, wherein the zero air has a relative humidity of from about 5% or less.

15. The method of claim 1, wherein the flowing carrier gas comprises nitrogen.

16. The method of claim 1, further comprising the step of testing a chemical detector with the analyzed mixture.

17. The method of claim 1, further comprising the step of changing the relative humidity conditions prior to analyzing the mixture.

18. The method of claim 17, further comprising the step of testing a chemical detector after changing the relative humidity conditions.

19. The method of claim 1, further comprising the steps of determining vapor pressure and compound volatility measurements prior to maintaining the reservoir at a sufficient temperature to form vapor from contaminants.

* * * * *